US008007543B2

(12) United States Patent
Martin

(10) Patent No.: US 8,007,543 B2
(45) Date of Patent: Aug. 30, 2011

(54) VACUUM ATTACHMENT SYSTEM

(75) Inventor: James Jay Martin, Oklahoma City, OK (US)

(73) Assignee: OrthoCare Innovations, Inc., Washington, DC (US)

( * ) Notice: Subject to any disclaimer, the term of this patent is extended or adjusted under 35 U.S.C. 154(b) by 0 days.

(21) Appl. No.: 12/440,581

(22) PCT Filed: Sep. 11, 2007

(86) PCT No.: PCT/US2007/019723
§ 371 (c)(1),
(2), (4) Date: Mar. 9, 2009

(87) PCT Pub. No.: WO2008/033337
PCT Pub. Date: Mar. 20, 2008

(65) Prior Publication Data
US 2009/0281637 A1   Nov. 12, 2009

Related U.S. Application Data

(60) Provisional application No. 60/843,969, filed on Sep. 12, 2006.

(51) Int. Cl.
*A61F 2/80* (2006.01)
(52) U.S. Cl. ........................................................ 623/34
(58) Field of Classification Search ............... 623/27–38
See application file for complete search history.

(56) References Cited

U.S. PATENT DOCUMENTS

| 0,980,457 | A | 3/1911 | Toles |
| 2,696,011 | A | 12/1954 | Galdik |
| 2,808,593 | A | 10/1957 | Andersen |
| 5,258,037 | A | 11/1993 | Caspers |
| 5,376,131 | A | 12/1994 | Lenze et al. |
| 5,549,709 | A | 8/1996 | Caspers |
| 5,658,353 | A | 8/1997 | Layton |
| 5,702,489 | A | 12/1997 | Slemker |
| 5,724,714 | A | 3/1998 | Love |
| 5,728,170 | A | 3/1998 | Becker et al. |
| 5,735,906 | A | 4/1998 | Caspers |
| 5,888,230 | A | 3/1999 | Helmy |
| 5,904,722 | A | 5/1999 | Caspers |
| 5,980,577 | A | 11/1999 | Radis et al. |
| 6,063,125 | A | 5/2000 | Arbogast et al. |

(Continued)

FOREIGN PATENT DOCUMENTS

WO   WO2008011548   1/2008

(Continued)

OTHER PUBLICATIONS

Limbogic VS Prothetist's Guide; Product Guide; Jun. 12, 2008; PN-2025-H; Ohio Willow Woods, Mt. Sterling, Ohio.

*Primary Examiner* — Bruce E Snow
(74) *Attorney, Agent, or Firm* — Black Lowe & Graham PLLC

(57) ABSTRACT

A vacuum socket system pertaining to the field of prosthetics wherein an enhanced suspension mechanism is provided by incorporating a vacuum source, circuitry, and a power source. A virtually air-tight seal between residual limb and prosthesis allows a vacuum fit to be generated via a vacuum source. The vacuum source is in constant interaction with circuitry and software for a means of vacuum pressure control, data recordation, and other means. A sound dampening method is employed to lessen both the sound and vibration generated from the vacuum source.

12 Claims, 8 Drawing Sheets

U.S. PATENT DOCUMENTS

| | | |
|---|---|---|
| 6,231,616 B1 | 5/2001 | Helmy |
| 6,287,345 B1 | 9/2001 | Slemker et al. |
| 6,508,842 B1 | 1/2003 | Caspers |
| 6,554,868 B1 | 4/2003 | Caspers |
| 6,645,253 B2 | 11/2003 | Caspers |
| 6,726,726 B2 | 4/2004 | Caspers |
| 6,761,742 B2 | 7/2004 | Caspers |
| 6,923,834 B2 | 8/2005 | Karason |
| 6,926,742 B2 | 8/2005 | Caspers et al. |
| 6,974,484 B2 | 12/2005 | Caspers |
| 6,979,355 B1 | 12/2005 | Slemker |
| 7,025,792 B2 | 4/2006 | Collier |
| 7,025,793 B2 | 4/2006 | Egilsson |
| 7,150,762 B2 | 12/2006 | Caspers |
| 7,393,364 B2 | 7/2008 | Martin |
| 2001/0005798 A1 | 6/2001 | Caspers |
| 2002/0087215 A1 | 7/2002 | Caspers |
| 2003/0078674 A1 | 4/2003 | Phillips |
| 2003/0191539 A1 | 10/2003 | Caspers |
| 2004/0167638 A1 | 8/2004 | Caspers |
| 2004/0181290 A1 | 9/2004 | Caspers |
| 2004/0260403 A1 | 12/2004 | Patterson et al. |
| 2005/0131549 A1 | 6/2005 | Caspers |
| 2005/0143838 A1 | 6/2005 | Collier |
| 2005/0197611 A1 | 9/2005 | Taranow |
| 2005/0240282 A1 | 10/2005 | Rush et al. |
| 2006/0212128 A1 | 9/2006 | Nachbar |
| 2006/0212130 A1 | 9/2006 | Collier |
| 2006/0282174 A1 | 12/2006 | Haines |
| 2006/0282175 A1 | 12/2006 | Haines et al. |
| 2007/0055383 A1 | 3/2007 | King |
| 2007/0112439 A1 | 5/2007 | Panucialman |
| 2007/0191965 A1 | 8/2007 | Colvin et al. |
| 2008/0004714 A1 | 1/2008 | Lieberman |
| 2008/0147202 A1 | 6/2008 | Danzig et al. |
| 2008/0221706 A1 | 9/2008 | Scussel et al. |
| 2008/0243266 A1 | 10/2008 | Haynes et al. |

FOREIGN PATENT DOCUMENTS

| | | |
|---|---|---|
| WO | WO2008033337 | 3/2008 |
| WO | WO2008073286 | 6/2008 |

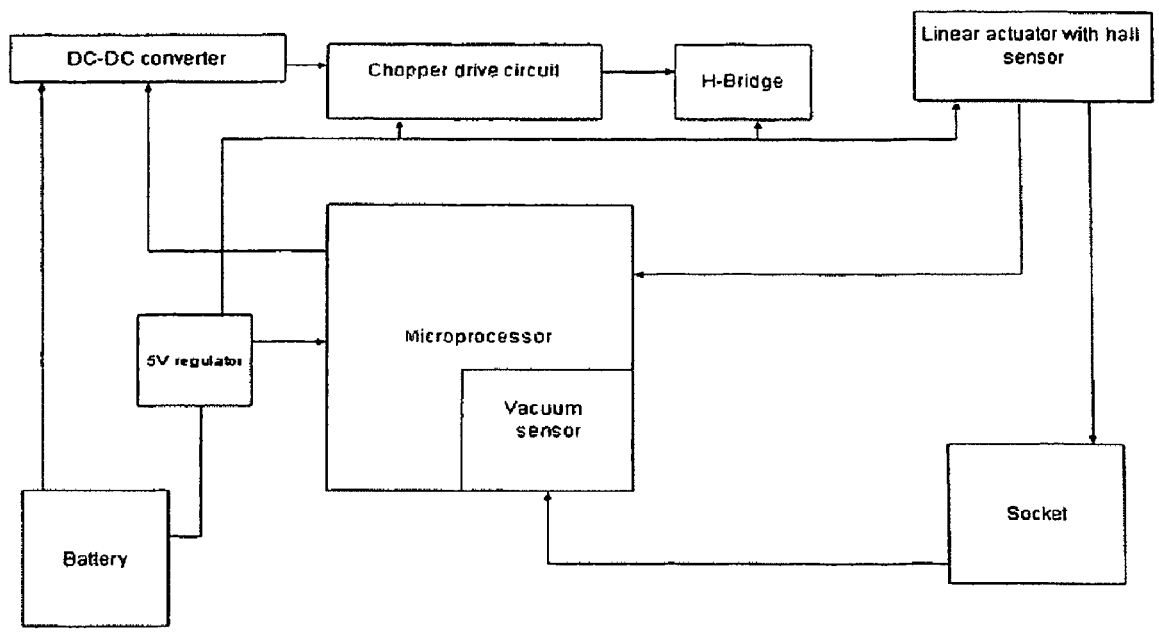
Fig: 8

VACUUM ATTACHMENT SYSTEM

PRIORITY CLAIM

This application is a national phase of PCT/US07/19723 filed on Sep. 11, 2007, which claims priority to U.S. Provisional Application Ser. No. 60/843,969 filed Sep. 12, 2006, the contents of which are hereby incorporated by reference.

FIELD OF THE INVENTION

In general, the present invention relates to a new and improved prosthetic socket system. More particularly, the present invention provides a vacuum system that is applicable in both upper and lower amputee prosthetic socket system which evacuates the air from the space that exists between the limb and socket and/or gel liner of the wearer, and/or between the liner and socket, and/or between the inner and outer gel liner. Furthermore, the device may be used to ensure an appropriate fit and secure suspension through the use of a circuit, pump, embedded software, and power means. By incorporating into the device the ability to record, monitor, analyze, and ultimately maintain a vacuum fit, a user friendly application will be generated.

DESCRIPTION OF PRIOR ART

The field of prosthetics, in general, has made great advancements in improving amputee and congenitally deformed individuals' performance on multiple levels through improvements in the design and incorporation of various prosthetic devices. Through these advancements, people across the world are experiencing new aspects of life and reaching new heights of applicability never before thought possible. Still, it stands to reason that the prior art continues to be deficient on numerous levels as will be discussed in greater detail below.

In modern prosthetics, the socket is the direct interface between the prosthesis and the user. In prosthetics, "suspension" is the term used to describe how the socket and residual limb are fixed to one another. It stands to reason the more firm the suspension method the more effective and efficient the prosthetic limb is. Some common methods of suspension include using a suspension sleeve, a locking pin mechanism, a corset, or a suspension belt. Each of these systems have there limitations in versatility and performance. One relatively successful method currently in use in the field of prosthetics has been using a vacuum system. This system conventionally uses a combination of a suspension sleeve to create an air seal between the prosthesis and the limb, and a small mechanical pump activated during the normal gait cycle to pull a vacuum pressure of up to at least 15 inches Mercury on the residual limb of the amputee from the socket.

The use of a vacuum system has benefits of far superior suspension compared to most conventional methods, and it has been found to promote good health of the residual limb itself through increasing circulation. The vacuum systems however have several limitations which are targeted by the preferred embodiment of this patent. Some of these limitations include poor cosmetic appearance, lack of versatility, heavy weight, high noise, poor usability, and poor replication of natural human locomotion due to the vertical shock of mechanical pumps or other non-biomechanical movements necessary to initiate pump actuation.

A preferred embodiment of this disclosure will eliminate these problems and allow superior suspension not only to transtibial patients, but all amputees, with both upper and lower amputations. A more cosmetic appearance will be allowed with the preferred embodiments disclosed due to its small size and ability to be cosmetically covered, even within a prosthetic pylon. Additionally, it will not require the user's weight or movement to initiate its actions.

A consistent problem that occurs with amputees is the volumetric change within the residual limb. This change in limb volume is caused by the flow of fluids to or from the limb. This presents problems for fitting prosthetic devices because a variable volume can lead to slippage of the prosthesis. By incorporating a vacuum pump, and hence reducing or eliminating the space that exists between the residual limb and the prosthetic device and also increasing the surface contact area, it is possible to control and maintain a fairly consistent volume within the residual limb throughout daily use.

A device, such as the one discussed in U.S. Pat. No. 5,724,714, uses an inflatable bladder within the socket. This method pumps air into or from the bladder to best fit the user. While this approach often leads to a comfortable fitting, it incorporates the use of a dual-socketed system which adds both bulk and weight to the total prosthetic device. This design exposes only certain points of the residual limb, predetermined to be weight-bearing, to the air bladder which over time can lead to residual limb swelling and traumatization. Furthermore, this method does not prevent limb volumetric changes, but rather attempts to account for changes in the residual limb.

Inflatable bladder devices also do not provide the same level of suspension as a vacuum system. It is observed that the device disclosed in U.S. Pat. No. 5,724,714 does not.

Help to prevent fluid loss or swelling in the limb but rather adjust the inflatable bladder to better fit the stump once this phenomenon occurs.

U.S. Pat. Nos. 5,549,709 and 6,231,616 disclose inventions that incorporate a vacuum within a multi-socketed system. These devices, however, do not incorporate any software control of the vacuum system and do not have intelligent manipulation of the socket environment. Additionally, they do not incorporate a means of recording environmental changes or use of the device, amongst others.

It is desirable to provide a self-sustainable design that monitors and maintains the vacuum pressure between the user and prosthesis. Additionally, to have a design that can record and analyze the data that is fed to it will allow for optimum usability for the wearer. Usability is of prominent concern in prosthetics, and to be able to circumvent constant monitoring of the device by the user is a key factor in socket design.

There are models in the prior art such as sold under the trademark eVAC which aim to promote a vacuum in the space that is formed between the gel liner and prosthetic socket by electronic means. This device, however, does not have a mechanism for recording the user data and does not have intelligent control of the socket environment—it only adjusts to preset settings. Furthermore, the device, when running, may be noisy which detracts from its potential applicability under certain instances.

U.S. Pat. No. 6,926,742 incorporates a mechanism for detecting and correcting a drop in pressure. It does not, however, provide a mechanism for recording the usability factors that incur with everyday usage of a prosthetic device. It also provides no sound dampening mechanism to counteract the noise that occurs when the pump(s) or motor(s) are turned on.

What is needed is a vacuum socket system applicable in prosthesis design that integrates the use of a circuit, pump, and power means. Furthermore, this design needs to be user friendly. It should incorporate a sound dampening mechanism to control the sound output from the device. Still furthermore, it needs to include a means of data collection. This data, when processed, will allow the device to be better tailored for each individual user. Furthermore, it should incorporate a means of actively altering the vacuum level by user and/or prosthetist and/or by the electronics and software corresponding to the environmental changes. Still yet, this device should be small, lightweight, and easily concealed within a prosthesis for optimum cosmetics.

SUMMARY OF THE INVENTION

In view of the foregoing disadvantages inherent in the known types of prosthetic socket system now present in the prior art, the present invention provides a new and improved prosthetic socket system for greater fit, comfort, and user needs. As such, the general purpose of the present invention, which will be described subsequently in greater detail, is to provide a new and improved prosthetic socket system which evacuates the air from the space that exists between the limb and socket and/or gel liner of the wearer, and/or between the liner and socket, and/or between the inner and outer gel liner.

To attain this, the present invention essentially comprises a vacuum system that is applicable in both upper and lower amputee prosthetic socket system which evacuates the air to ensure an appropriate fit and secure suspension through the use of a circuit, pump, embedded software, and power means. By incorporating into the device the ability to record, monitor, analyze, and ultimately maintain a vacuum fit, a user friendly application will be generated.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved prosthetic socket system which may provide a constant or as desired vacuum between the user and the prosthetic and allow an amputee to attain a safer and more comfortable fitting, have better proprioceptive control, and feel as though the prosthesis is an extension of the user's own body.

It is a further object of the present invention to provide a new and improved prosthetic socket system which is of a durable and reliable construction and may be utilized with upper and lower prosthetic applications.

An even further object of the present invention is to provide a new and improved prosthetic socket system which is susceptible to a low cost of manufacture with regard to both materials and labor, and which accordingly is then susceptible to low prices of sale to the consuming public, thereby making such economically available.

Still another object of the present invention is to provide a new and improved prosthetic socket system which provides all of the advantages of the prior art, while simultaneously overcoming some of the disadvantages normally associated therewith.

Another object of the present invention is to provide a new and improved prosthetic socket system with relatively minor user training, consistent performance, and provides relatively no or minimal noise.

An even further object of the present invention is to provide a new and improved prosthetic socket system which allows for user feedback.

Still another object of the present invention is to provide a new and improved prosthetic socket system which may be adapted to existing prosthetic uses and applications.

Yet another object of the present invention is to increase user comfort and decrease known medical risks associated with prosthetic as well as increase user comfort in general.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference would be had to the accompanying drawings and descriptive manner in which there are illustrated preferred embodiments of the invention. Furthermore, it should be noted that while much of the descriptions of this patent are referencing prosthetic device usage, the system may easily benefit other applications where a vacuum source is required, and should not be considered limiting to prosthetics

BRIEF DESCRIPTION OF THE DRAWINGS

The invention will be better understood and objects other than those set forth above will become apparent when consideration is given to the following detailed description thereof. Such description makes reference to the drawings in wherein:

FIG. 8 is a general block plan of a preferred embodiment.

DETAILED DESCRIPTION OF THE PREFERRED EMBODIMENT

Figure 1:
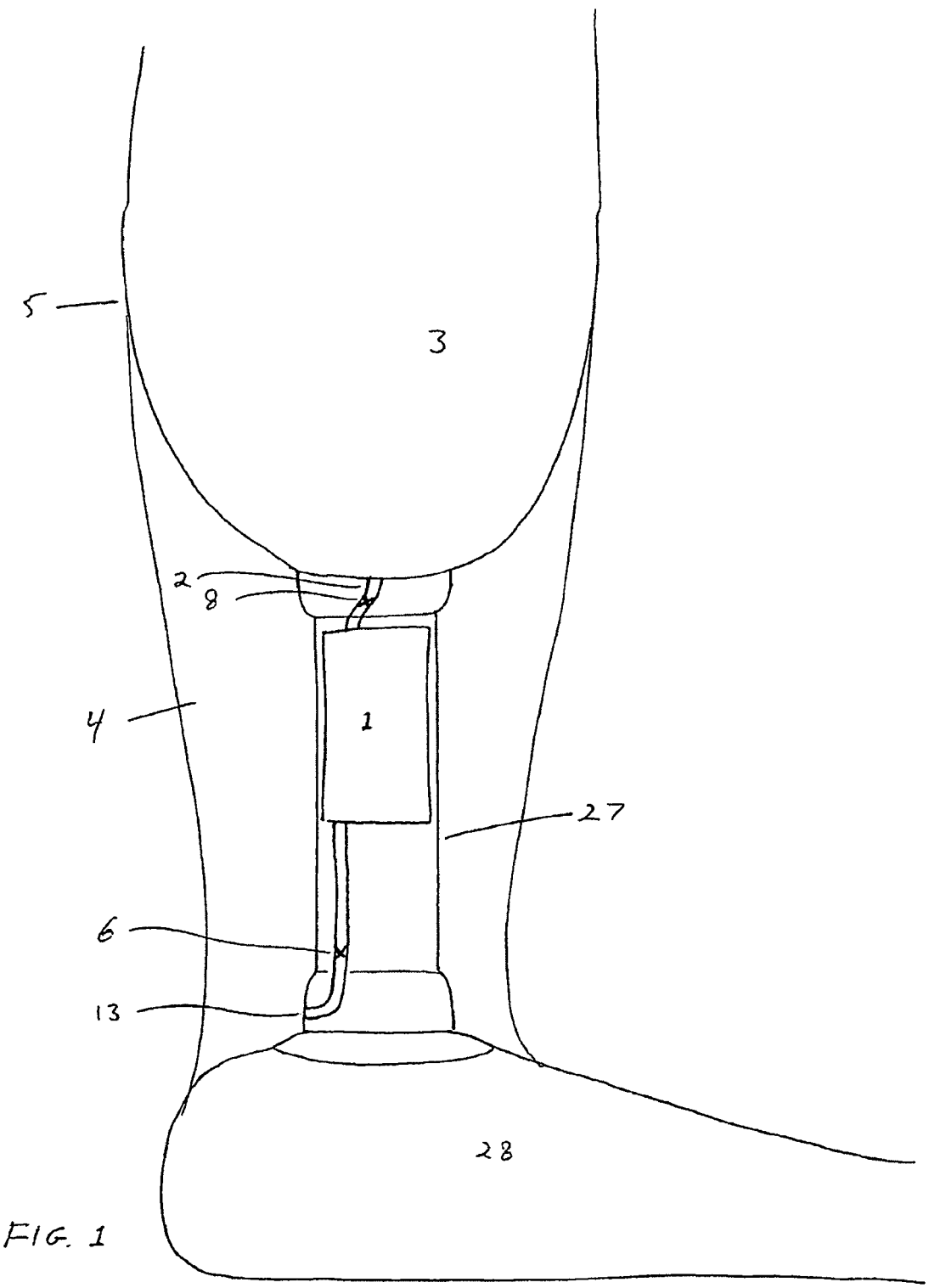
FIG. 1 is a general side view of a preferred embodiment.

This disclosure, in general, describes a new and improved vacuum socket system which provides enhanced suspension and, in turn, a more effective and efficient prosthetic limb application. In prosthetics, "suspension" is the term used to describe how the socket and residual limb are fixed to one another. By improving this suspension mechanism, an amputee may attain a safer and more comfortable fitting, have better proprioceptive control, and feel as though the prosthesis is an extension of the user's own body.

Without the intention of limitation, the present invention may generally comprise a pump or series of pumps, a circuit, control software, and a power source for the implementation of a new method of suspension. The invention is used to evacuate air from the space that exists within a socket system which in turn ensures a secure fit and improved suspension.

A key factor in the device is the necessity for a complete or near complete air tight seal between the prosthesis and the body. This is achieved by utilizing a sealing suspension sleeve, dual layer liner, or other methods of sealing such as using a self sealing liner, compression ring, or other forms of sealing. Around the residual limb there may be a gel liner that is partially covered with a sock, hose, or other porous covering so that the top few inches may be exposed. The porous covering may allow air to wick within the socket so that a uniform vacuum may be achieved. The socket should fit securely around the liner and porous covering. A nonporous suspension sleeve or other sealing methods will initially hold the socket to the leg, sealing against the socket, gel liner, and skin of the user. This is a virtually air tight system that ensures the greatest efficiency for the device.

Vacuum is pulled from the socket via a small hole and/or an air-permeable area of the socket, protruding from the socket. It is essential that no leak exists within the connection between the hole in the socket and the vacuum system. Within this connection may be a filter that prevents any extraneous particles from entering the vacuum pump. If this were to occur, the particles could potentially harm the efficiency of the vacuum system. In addition to this, a one-way valve may be incorporated to promote and retain the vacuum within the socket. The one-way valve allows air to exit the socket but not re-enter.

The vacuum itself may be generated by a pump system. The pump system could include several possible configurations such as but not limited to: linear actuator driven pump, artificial muscle driven pump, electro-active polymer or other material driven pump, any other non-motor driven pump, one electric diaphragm pump in series, two electric diaphragm pumps in series, or any other configuration that may provide the necessary power input to yield a device that does not stray from the scope of the invention as disclosed. Furthermore, any type of pump other than a diaphragm pump may be utilized as well. Essentially, any electronically and/or non-electronically driven method of air evacuation may be utilized via the aforementioned setup.

The system may as well use foam or similar vibration damping means around the motor or housing to additionally minimize the sound. This method also may allow for accommodation of varied inner diameter of prosthetic pylons, while maintaining the ability of the unit to fit inside of such.

Due to the noise generated from the application of a pump, a sound proofing method or methods may be utilized. There are several methods that may be employed. These could include but are not limited to wrapping sound proofing foam around the pump(s) or motor(s), encapsulating the pump(s) or motor(s) with a sound dampening material such as silicon or any other material capable of dampening sound waves, or even possibly fixing a type of silencing device to the vacuum system. Further sound reduction may be achieved by affixing or encompassing a cosmetic covering or casing to the outside of the pump system which may reverberate the noise in directions other than outwards, or simply dampen the sound generated from the pump. Additionally, the use of mass encasement encompassing the pumps, preferably in an airtight manner, may be used to dampen the sound transmission through the encasement. Additionally, the use of vibration damping methods such as but not limited to a wrap, fiber, or other similar highly vibration damping methods may be utilized. The pump may be encompassed by these, or similar materials to prevent vibration, and then encompassed in an encasement of sufficient mass to prevent sound transmission. Alternatively, or in conjunction, the encasement itself may have a vacuum drawn in it about the pumps, to prevent sound transmission—since sound can not be transmitted through a vacuum (given that no vibratory effects are the cause of sound transmission). Vacuum may be drawn by the pumps for both the socket and the encasement. Additionally, a simpler concept of sound and vibration dampening may involve slowing down the pump actuation or gearing motor, or simply using a low noise actuator to draw the pump may be used.

Additionally, the encasement for the pump system may include other prosthetics components such as a pylon or housings of other prosthetic devices. Typically, the pylon is of a round, hollow nature and aids in the support and strength of the prosthesis structure. Because of its hollow nature, the space within the pylon is rarely utilized in useful application. The use of a pylon, for instance, allows for the mass of the already existing component to be used for sound mitigation, for sound mitigation is related to the mass of the housing. This enables for a very lightweight vacuum system to be used, and utilize the pylon for both sound mitigation and structural protection. Additionally, the unit may use the inner wall of the pylon as the piston housing.

A preferred embodiment may include several possible pressure controlling mechanisms. One such method is to incorporate a variable vacuum switch with a fixed dead band. Hypothetically, if the device is to maintain a vacuum of 21 in Hg within a range of 4 in Hg, the vacuum level must be monitored and have the ability to turn on and off at the appropriate time. By setting a fixed dead band, the vacuum pressure will increase to a level of ideality wherein the vacuum system will be disabled. As the vacuum pressure slowly diminishes, it will reach a threshold wherein the fixed dead band is reached and signals to the vacuum system to reactivate and begin generating a vacuum once again to the level of ideality. This process allows for the vacuum to be operated only under necessary measures in order to conserve energy and reduce operating noise.

Another pressure controlling mechanism may involve using a pressure sensor. This pressure sensor may be incorporated into a microprocessor controlled system wherein a range of pressure limits would be set. When in the set pressure range the pump would be deactivated. Once the limits are reached the pressure sensor detects the shift and relays an analog, or other, signal to the microprocessor unit which in turn relays a signal to the vacuum pump to activate once again. The range of vacuum pressure may be adjustable depending on the nature of individual vacuum requirements. Additionally, the top and bottom threshold of the pumps actuation may be independently adjusted through multiple means including but not limited to—electronic resources, manual resources, dials, switches, sensors, graphic user interface, etc.

In addition, corresponding to the force applied to the prosthesis, the top end level of vacuum may be actively adjusted in order to provide a greater suspension to the limb. This variability in the vacuum levels may be pre-set, or correspond to algorithms in the control system, or both. For instance, when the user of an upper extremity vacuum system picks up an object of sufficient mass, the vacuum system reads that a load has been applied, and that the prosthetic limb is tending to be pulled away from the residual limb. This initiates the vacuum source to turn on, increasing the level of vacuum, and providing greater suspension.

Furthermore, a means of data recordation may be incorporated within the device. This may be achieved by equipping a circuit board with a microprocessor or microcontroller unit within the system. This electronic unit receives data from the pressure sensor and in turn processes it and records in via digital, or other, means. This recorded database may then be accessed by an external computer or other device which may process the information. By doing this, each prosthetic device can be tailored to the usability needs of each individual based on the day to day activities that the individual partakes in. The external computer could communicate with the vacuum system by multiple methods including but not limited to a USB port or via a wireless signal, such as Bluetooth or other means. The wireless signal would allow both the user and prosthetic fitter much easier access to the data acquisition in the unit, as well as means of adjusting and setting the parameters of it. The wireless method may be activated for a given, or settable, period of time after the unit has been disconnected from a power source, or turned on, or other methods of defining a given usability moment which may initiate the use of the wireless communication system. Additionally, the attachment of the power source may automatically download information from the prosthesis to another storage or computer device.

A software and Graphical User Interface (GUI) system may also be incorporated. This system may be in direct interaction with the circuit board and microprocessor. The software system may include a multitude of options and functions. These can include but are not limited to keeping track of a database of the patient name and additionally the date and time that the patient was last adjusted or observed by the prosthetist, as well as record the date and time of use information of the user. The software may additionally retrieve settings from the prosthesis circuitry and microprocessor and update this information with new settings. The system settings may include a setting for changing the minimum vacuum pressure that the prosthesis can be at before the vacuum pump is to restart. Furthermore, a maximum vacuum pressure may be set, indicating an upper limit under which the prosthesis can maintain its fit to the residual limb for normal use, and can use alternative thresholds/algorithms for specialty use such as but not limited to greater force being exhibited on the prosthesis as discussed before. Additionally, the control program may incorporate a system that monitors temperature and/or humidity/perspiration within the socket environment, and consequently initiate the pump based on these or other parameters. This may incorporate additional sensors to determine such parameters for adjustment. Even furthermore, the system may incorporate a novel systematic method of variably adjusting the vacuum level throughout the day in order to promote circulation in the limb. This may provide a greater and lesser vacuum level to be drawn throughout the day so that the tissue experiences force changes on the limb and increased blood flow.

Even furthermore, a setting for the time period of pressure check frequency and data record frequency may be included. These allow the prosthetist to view various graphical representations of the vacuum pressure change over various time limits. This data is crucial as it indicates the average period of time under which an acceptable vacuum hold is maintained and ever further may indicate whether or not a leak or malfunction in the vacuum system exists. The software allows the prosthetist to monitor multiple patients in the respective patient database. Additionally, the software allows the user to select a method of low battery alarm, which may include an indicatory vibration, audible beep, or other methods.

A power supply may be derived from a multitude of sources. The device could include a rechargeable battery that may be recharged without the necessity of removing the battery from the device itself. This would prove to be beneficial in terms of both maintenance and applicability. Additionally, an internal battery may not be necessary as the device could be designed to draw power from a central power source located within the prosthesis that would power the vacuum device in addition to the other prosthetic components. Additionally, a power recharging unit that does not require direct contact may be utilized to provide additional protection from environmental damage, such as water. Furthermore, a means of low battery indication may be incorporated. Even furthermore, battery charging capabilities may be incorporated within the device. A multitude of charging options may be utilized including a hidden electrical outlet within the device or even possibly an underlying USB port that can be in connection with a computer as a charging source, as well as power generation strategies within the device. It is further understood that more charging methods other than the aforementioned may be incorporated into the device.

The preferred embodiment may also include an easily operated on and off switch. The switch may be mounted inside the socket so that when the prosthesis is dawned the device will automatically trigger. Other options include but are not limited to putting the switch on the exterior of the socket so that when the sleeve is appended the switch is activated, and also locating the switch beneath the cosmetic covering so that it may be activated by intended contact with the user. Additionally, the unit may use automatic on/off switching capabilities through means such as but not limited to motion sensor, wherein the system turns on for a period of time after slight movement of the system takes place, and off after period of time of no movement. The system may as well turn off automatically after a period of time of the pumps running with no significant change in vacuum level. Furthermore, an additional backup on/off strategy may be employed within the system, such as but not limited to: key chain type remote, blue-tooth, cell-phone activated, or other. Still furthermore, the system may monitor general motion of the limb to initiate, sustain, or adjust the vacuum level or socket environment. For instance, as the user may be more active, the vacuum level may increase to account for that increased activity. This may use sensors such as but not limited to force, step counter, cadence variance related information, time clock, angle, angular change, angular velocity, accelerometer, or other known sensors found in the field of prosthetics and robotics.

Generally, the vacuum system could include but is not limited to a piston or hydraulic mechanism, gear system or linear actuator, vacuum chamber, valves, power means, and a resource for monitoring and controlling the pressure variations within the socket, using the space itself to create the pump. It may also utilize a diaphragm, rotary, or other pump system placed within the cavity.

A diaphragm pump, rotary pump, or axial pump may be assembled in the same manner as previously mentioned, but simply within the pylon. The unit of pump(s), electronics, and charging device may be mounted within the pylon to further save space within the prosthesis. All electronics and circuitry may be configured in such a manner that they fit within the pylon and easily mounted on a mounting system. Additionally, a method of affixing exiting wires and air tubes to the unit so that they, in addition to the vacuum system, do not slide up and down with the movement of the prosthesis. Wires and tubes may as well exit the pylon as necessary to provide usability. The system as a whole, preferably, would be water and wear resistant, and the method of placing the system within a pylon may lend to that goal.

Incorporating an axial pump may be beneficial due to the powerful nature under which a piston can operate. It is contemplated the necessary pressure needed to facilitate a vacuum may be generated with only a few strokes of the piston. Not only could this possibly elongate the life of the power means, but it would also minimize any extraneous noise generated by the pump due to very low vibrations.

A piston may be utilized within the axial pump. The piston head, to create an optimal vacuum, may lay flush with the inner wall of the pylon or accessory housing. While not limited to, it is proposed that the piston head may be made of a material that is conventionally used in piston heads. By using certain materials, the piston head will remain in solid contact with the inner wall while still being able to adjust and conform to the necessary configurations required of each upward and downward piston movement. It may alternatively utilize other conventional piston types of design.

The piston may move in the axial manner via any number of methods including but not limited to a helical worm gear system or linear actuator. A helical worm gear system operates in constant connection with the motor which may be of a rotary fashion. This may as well include a "reverse-double helix internal sliding glider hollow piston pump" or other known methods. Additionally, the helical worm gear may be attached to a piston which moves in relation to the movement of the helical worm gear. As the rotary motor turns it rotates the helical worm gear system in an upwards fashion and in turn forces the piston to move upwards. Once a full movement of the piston has been made a mechanism such as but not limiting to a clutch may be employed to allow for the downward motion of the piston to its starting position.

A linear actuator works similarly to a hydraulic pump. Rather than using hydraulic fluids, the linear actuator utilizes an electrical motor and/or other means. The inner shaft of the linear actuator may be in contact with, and generate the force necessary to raise and lower the prior mentioned piston, which under a tight fit generates the necessary vacuum. Alternatively, hydraulic actuators may be employed to initiate movement of the piston, or other pump methods. In some cases, the prosthesis may already use a hydraulic pump for other joints, and may be able to capture the force and weight of the preexisting system to operate this device as well. A small valve system may be employed to control such a device.

In the space that exists above the piston lies the vacuum chamber. Depending on the force imposed by the piston, the pressure will fluctuate within the vacuum chamber based upon whether an upstroke or downstroke of the piston is occurring. Pressure on the upstroke is essential to force air out of the socket for the necessary vacuum requirements. In addition to this, a seal may be incorporated at both the bottom and top pylon in the area wherein an air-tight environment is conducive.

Located on the system may exist a one-way valve or system of one-way valves. Oneway valves act to restrict the flow of air into and out of the socket system. Without limitation, one-way valves may be placed within the vacuum chamber to control inward and outward airflow.

Furthermore, two-way valves may be required in the chamber below the piston to release any pressure formed from piston operation. If the pressure chamber was void of these two-way valves, pressure would build up from the amassed air preventing a downward stroke of the piston from occurring. Another possible method for rectifying this situation would be to have this chamber free-flowing and open to the atmosphere.

Still furthermore, the addition of nanotechnology may be implemented within the system for decreased weight, increased energy efficiency, decreased noise, or enhanced performance, among other things. Additionally, for instance, the use of super hydrophobic nano-technology may be implemented to decrease friction within the system, and increase energy efficiency. Other types of nanotechnology applied to such a prosthetic or medical pump device may be implemented, which may as well limit bacterial growth, amongst other benefits.

The unit may as well use an induction coil or other way to generate power or recharge the battery or may use power generated by movement, steps, or general activity.

Figure 6:
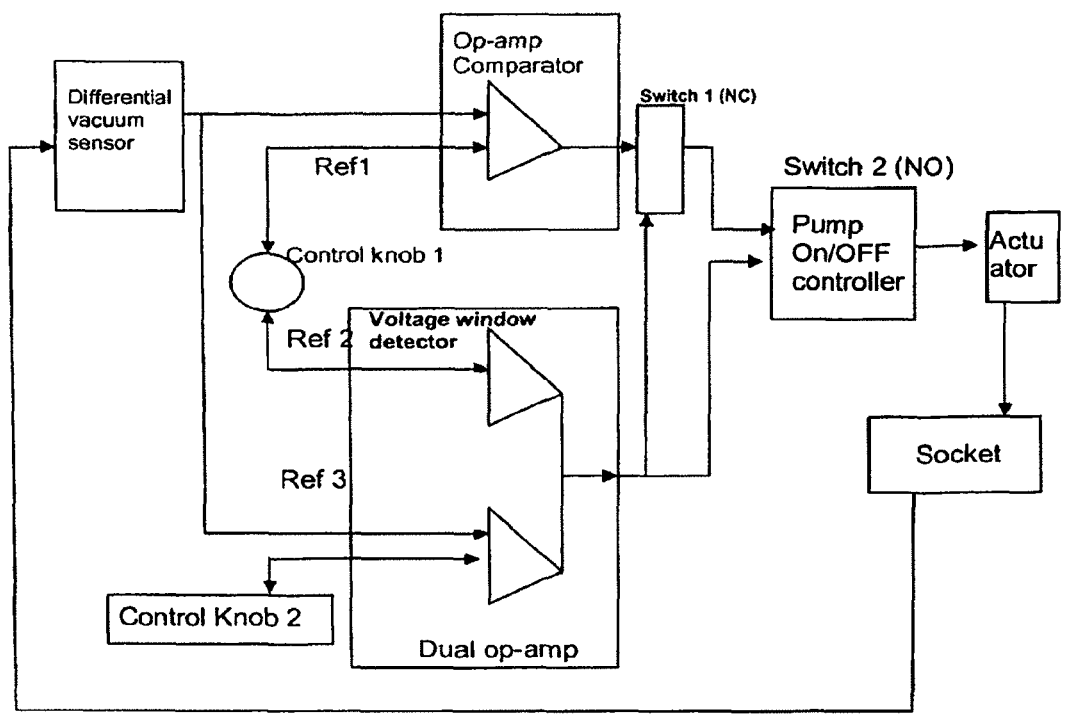
FIG. 6 is a general block plan of a preferred embodiment.
Figure 7:
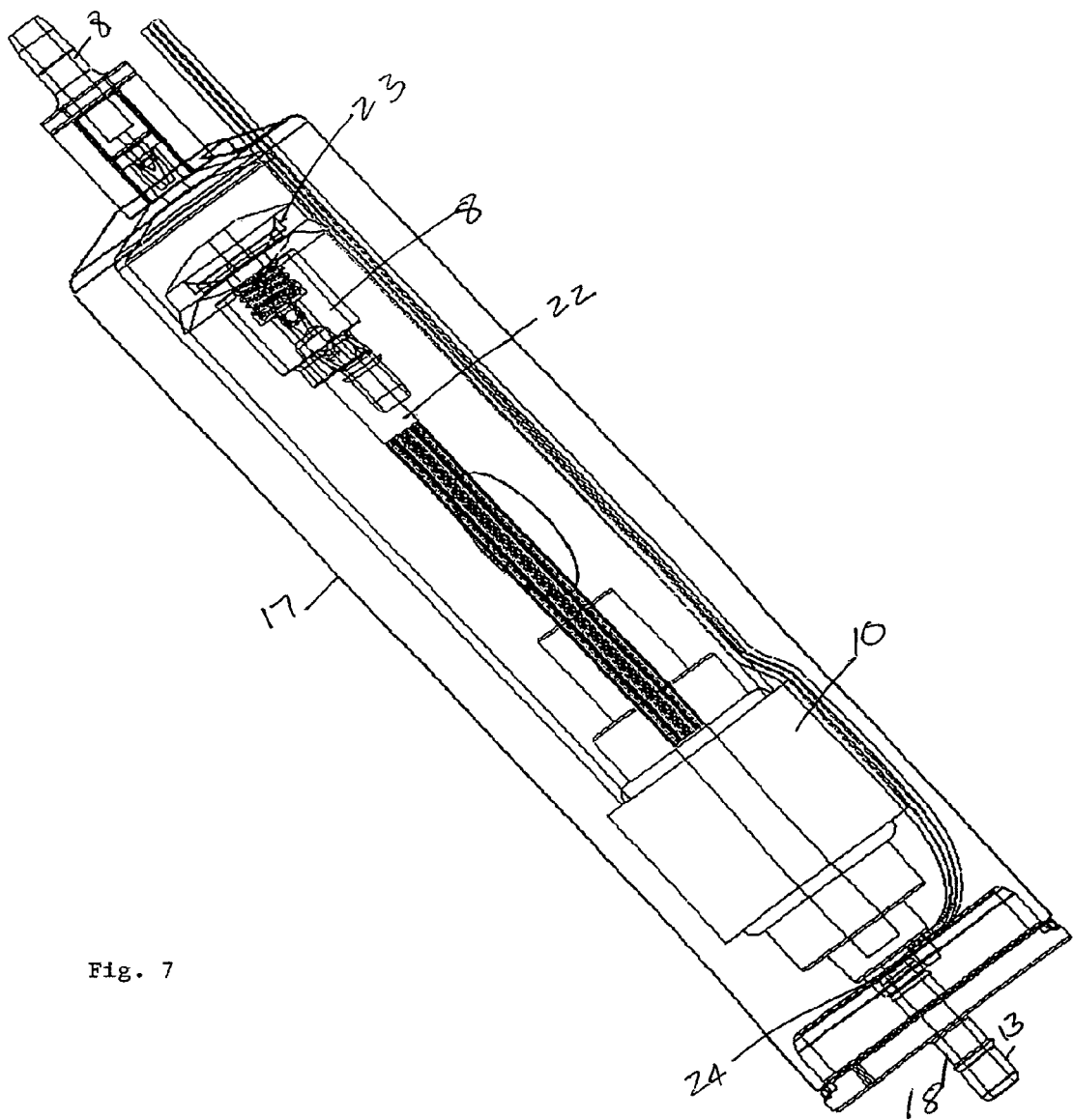
FIG. 7 is a general view of a preferred embodiment.

In another embodiment, a non-digital computer regulator system can be used for maintaining any chosen vacuum range in a prosthetic socket (see FIG. 6 below). User can set vacuum level through use of dials, knobs, or other sources to adjust desired vacuum range. The system may consist of combination of one, two, or more control circuits to set the lower and upper vacuum level range. The single op-amp comparator circuitry turns the actuator ON when the system is powered for the first time, for instance. The Ref 1 (reference voltage 1) and Ref 2 (reference voltage 2) in FIG. 6 may be at the same voltage. Knob 1 in FIG. 6 may set the lower vacuum level for the system. Knob 2 in FIG. 6 may set the upper limit of vacuum range. The prosthetist/user may set these knobs prior to starting the system. The knobs can also be adjusted while the system in on. There may be two switches in the system, or more or less. Switch 1 is 'Normally Close' type and switch 2 is 'Normally Open' type. The switch 1 may disconnect the startup circuitry as soon as the vacuum level reaches lower range value the voltage window detector circuitry may take over from there and controls the actuator to keep vacuum in range through switch 2 for instance. A differential vacuum sensor may be attached to the socket with one side to atmospheric pressure. The input from sensor may be fed to one or more circuits.

Still furthermore, the control of the system may utilize a wired or wireless communication various control systems, such as but not limited to computer, handheld computer device (such as possibly Palm Pilot or Blackberry type of systems), phone, watch, or other practitioner or user settable systems. These may be used to allow the practitioner or user to adjust setting parameters from time to time. In addition, the user may have a relatively limited number of options to adjust, whereas the practitioner or administrator of the device may have a broader range of use options.

FIG. 1 details a general side view of how the preferred embodiment may fit within a prosthetic limb of a transtibial prosthetic leg 5. This configuration may have similar applicability within other types of prosthetics and orthotics as well. The device 1 pulls air from a socket system 3 through a small hose or channel 2 that connect said device 1 and said socket 3. There is a one way air valve 8 that is placed between the socket and the vacuum device.

Furthermore, it is understood that that while the cosmetic covering 4 is not an essential component of the preferred embodiment, it is advantageous that device 1 be small enough to fit under said covering 4 when there is not enough space to fit it within the pylon 27. The pylon 27 typically fits between the foot 28 and the socket 3 for transtibial applications. It may be noted that device 1 has been designed to be applicable under many circumstances in addition to the transtibial prosthetic leg 5, such as but not limited to transfemoral, transradial, transhumeral, and various disarticulation methods, in addition to various orthotic levels. There as well exists an air exit method from the device 13. This air escape method is important to allow the air drawn from the vacuum to be dispelled from the prosthetic limb. This may be connected with a tube, or simply by the various materials of the limb having sufficient space for air to travel past. This method may as well incorporate a filter muffler 6 for better noise reduction.

Figure 2:
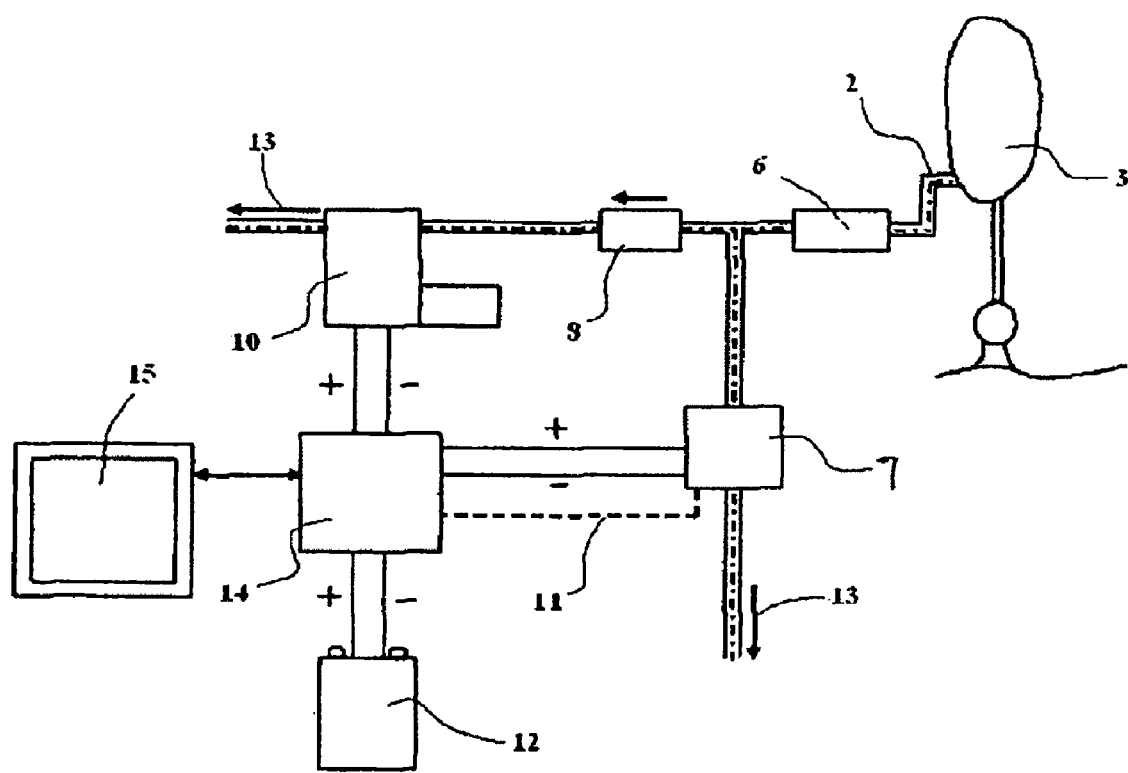
FIG. 2 is a general block plan of a preferred embodiment.

FIG. 2 details a general perspective expanded view of the preferred embodiment. This figure illustrates one of a multitude of arrangements for the components within device 1. This particular illustration shows a system in which air may be pulled through a hose 2 from socket system 3 and into a filter or membrane 6. The filter 6 acts to prevent extraneous particles from entering said device 1, as well as assists in noise reduction in exiting.

Filtered air may next pass through a one-way valve 8, which acts to keep air from reentering the socket 3 once it has been pumped out. It is understood that this air flow out of said socket is generated by a vacuum pump(s) 10 which then may cycle the air out of the device 1 through an exhaust valve 13. It is further understood that a series or set of pumps may be used depending on the necessary level of pull that needs to be generated for each application.

It is even further understood that said vacuum pump 10 need not be continually running when in the presence of said one-way valve 8. It is further understood that, depending on the configuration of the pump system 10 and pressure sensor 7, there may be one-way valves 8 additionally an other outer direction from those above-mentioned components. The pump 10 may be controlled by a circuit board which is transmitted signals from a differential pressure transducer or other means 7. The differential pressure transducer 7 operates in a manner such that a pressure difference is measured between the socket 3 and the outside air. From this, an analog signal (voltage) 11 is generated and relayed back to the circuit board, microprocessor, and/or other similar means 14 which processes the information. A signal from said circuit board etc 14 is generated and sent to the pump 10 relaying whether the pump needs to generate a stronger vacuum pull or not. The software control program as well analyzes the necessity of the pump to pull a stronger vacuum dependant on information such as experienced vacuum pressure from within the socket environment based off of forces, as well as perspiration and temperature information.

Furthermore, a power device such as, but not limited to, a battery 12 may be located within the preferred embodiment, or in an external manner wherein a single power device is used to power not only the device 1 but also other components incorporated within the prosthesis. The battery would power the circuit which in turn switches the power to the pump when necessary.

It is also suggested that the prosthesis and device be assembled in such a manner that the circuit board etc 14 can be linked to an external computer 15 for purposes of modification or other means. Depending on the patient's level of activity, a clinician may adjust the vacuum ranges to better suit particular needs, as well as determine usage information from stored data on the device 1.

Figure 3:
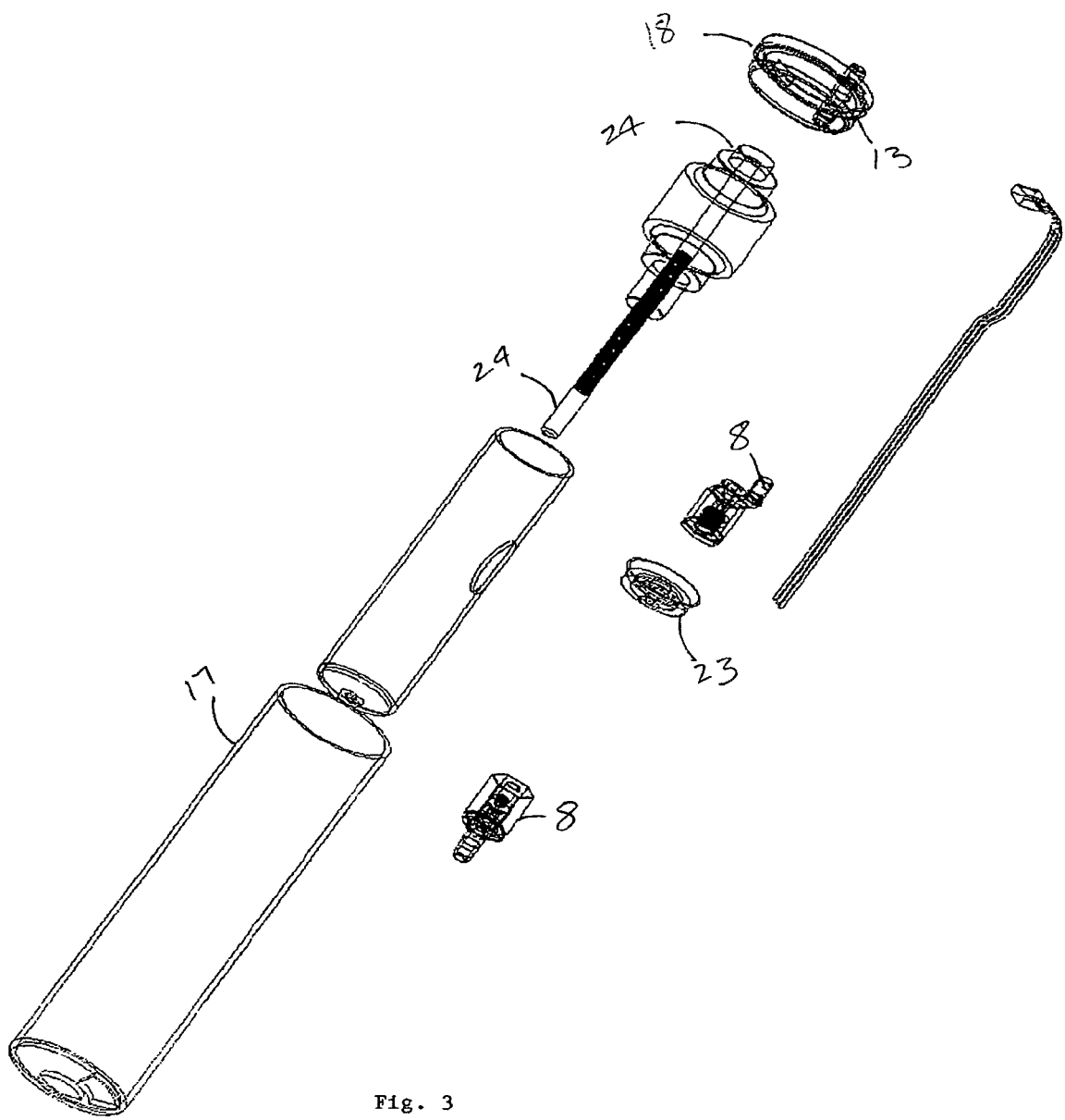
FIG. 3 is a general partially exploded cutaway view of a preferred embodiment of the invention.

FIG. 3 details a partially exploded cutaway view of a preferred general construction of the preferred embodiment. This illustration shows one of many possible configurations for the preferred embodiment. A linear actuator pump 10 is surrounded by some barrier or casing 17 which not only protects the confined inner-workings but also acts as a sound barrier to mute any auxiliary noise that may accompany the pumps 10. Additionally, this assembly may as well be located within an outer housing such as a cosmesis 4 or pylon 27 to further mitigate sound and vibration transmission. This casing 17 could be made out of any number of materials including, but not limited to, plastics, metals, ceramics, elastomers, and polymeric materials.

It is also understood that the casing 17 may have a detachable side(s) 18 making for easy access to the inner-workings such as the circuit etc 14, pump 10, and transducer/pressure sensor 7. Furthermore, it is contemplated that side 18 is attached to complete the entire casing 17 via attachment means such as but not limited to screws or press fit. It is understood as well that this detachable side may be secured in an airtight manner to further prevent sound damping. Additionally, casing 17 may fit snuggly into outer casing 27 with means such as a press fit, or other methods to help hold it securely in place. Additionally, there may exist a further sound transmission barrier between 17 and 27.

In addition to this, the casing 17 with said detachable side 18 may be outfitted with holes wherein a sound dampening material may be applied to aide in assimilation of noise production further produced from the pump 10 and its resonance within the housing 17. Materials may be but are not limited to sound dampening silicon, highly elastic polymer based materials, fibers, or other materials. Additional sound dampening methods may be employed through varying the mass of the casing 17 and 27 and utilizing various shapes of said casing 17 to best prevent sound transmission.

In a preferred construction, both a one-way valve 8 and an exhaust valve 13 may also be incorporated onto casing 17. It is also understood that a USB or similar port (not depicted) may be incorporated into device 1 allowing for easy communication between circuit etc 14 and an external computer. This ideally would circumvent the problem of having to disassemble the device 1 for service when necessary. This may as well utilize a wireless communication system instead.

Figure 4:
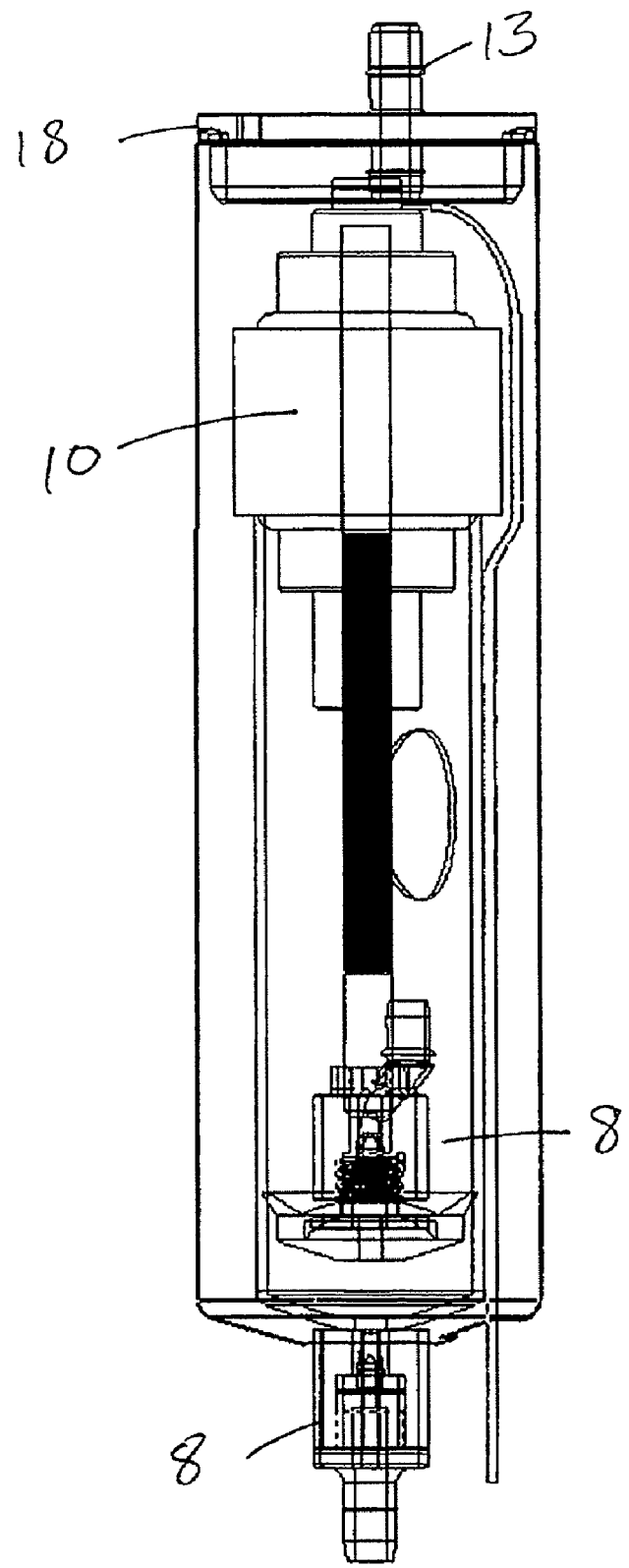
FIG. 4 is a general view of a preferred embodiment.
Figure 5:
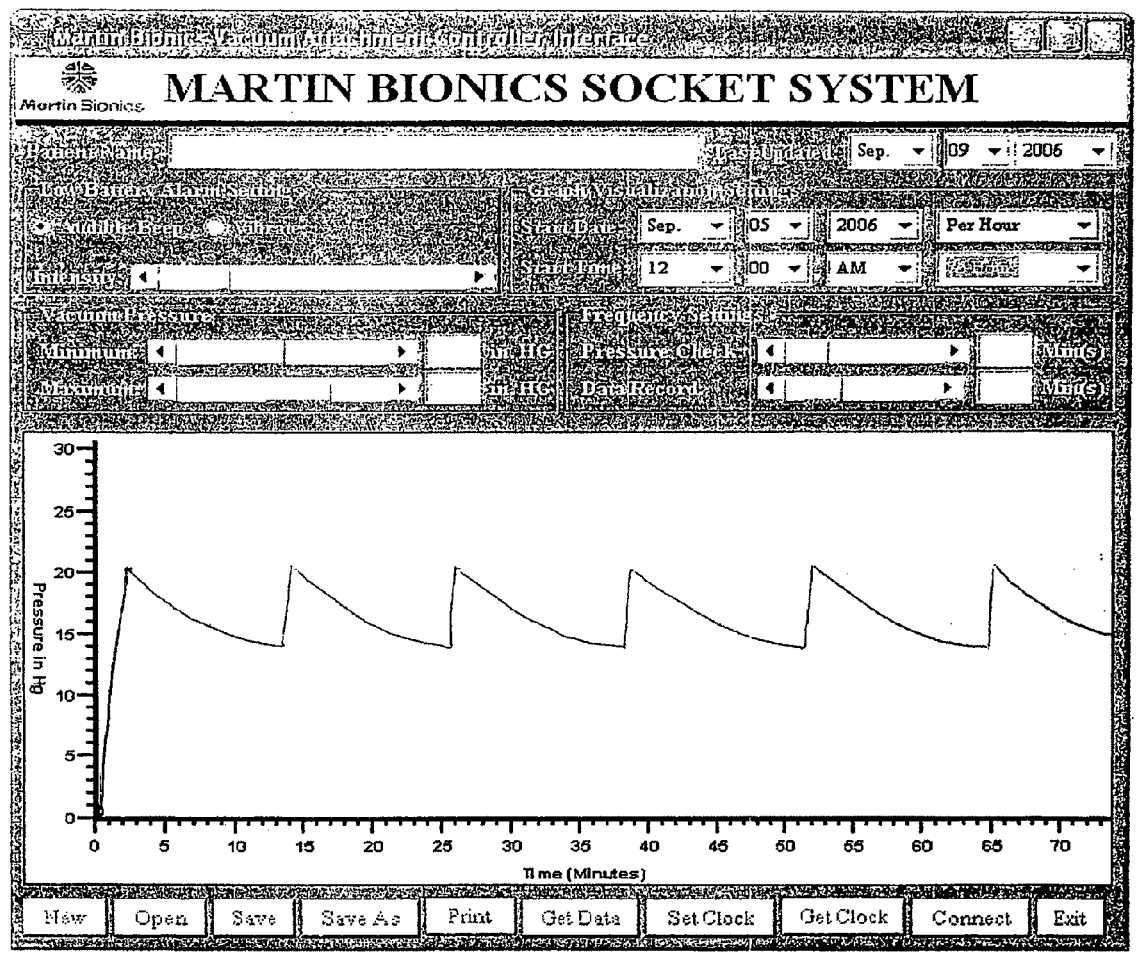
FIG. 5 is a general view of a graphic user interface that may control the settings of the device.

FIG. 4 is a general view of the preferred general construction and how the individual pieces fit within one another. The system may as well be sized to fit within a prosthetic pylon 27 directly, without housing 17. This method may utilize the prosthetic pylon 27 as the sole housing, further decreasing the overall system weight. The vacuum system may comprise ah pump 10 outfitted with a piston 22 and joint fittings 24. In addition to the outfitted pump 10 there may also be a plunger 23 or other vacuum sealing means. The plunger 23 acts to create an air tight seal wherein a vacuum may exist. The housing 17 and/or end caps 18 may incorporate one way valve(s) 8 to regulate air flow to and from the vacuum system. These may as well be at least partially incorporated within the plunger itself. Additionally, the housing 17 may contain a joint fitting(s) 24 wherein the pump 10 may be attached to help minimize vibration and other extraneous movements.

In prosthetics and orthotics, and more particularly pertaining to artificial limb prosthetics, a vacuum socket system wherein an enhanced suspension mechanism is provided by incorporating a vacuum which may be pressurized for donning purposes, may utilize a vacuum source, circuitry, and a power source.

The invention may include a sound dampening method.

The invention may include a sound decibel level of less than 50 dB that is achieved via said sound dampening method(s).

The invention may include circuitry in interaction with a Graphical User Interface (GUI) and a software system.

The invention may include circuitry additionally which is equipped with the ability to monitor and record various functions of prosthesis usability.

The invention may include a sealing mechanism such as a dual layer liner, or other sealing device which is incorporated to encourage a maximal vacuum environment.

The invention may include a vacuum source, wherein a vacuum is generated from said vacuum source that may be located internal within a pylon.

The invention may include a linear actuator or a linear piston pump or similar method to operate a pump. Additionally, an air-tight piston may be utilized.

The invention may include a vacuum source actuator which may be in direct contact with a piston. Additionally, this piston may be of the sealed, air-tight nature.

The invention may include a power source that may be incorporated within, or in addition to the apparatus. Additionally, the power source may be located externally to the apparatus as a central power source for multiple applications.

The invention may include a pressure controlling mechanism that may be utilized to control relative level of vacuum corresponding to applied forces, alter the socket environment according to environmental needs such as perspiration and temperature, and conserve power.

The invention may include an easily operated on/off switch that is incorporated, such as one that automatically shuts the system off when not in use.

The invention may include an off switch that is automatically operated through reduction in vacuum level for a given period of time with little to no effect from the vacuum pump(s).

The invention may include an electroactive polymer, artificial muscle, or similar actuator that may be used to operate the vacuum pump.

The invention may include existing prosthetic components that may be utilized as sound damping of the vacuum source.

The invention may include a non-digital computer regulator that is used for control, such as but not limited to adjusting the vacuum level and other functions.

The invention may include a microprocessor or digital computer that is used to sync the electronics and software of the system to a graphic user interface.

The invention may be interfaced with a graphic user interface through a wireless interface using single or multi-channel wireless communication system, including but not limited to blue tooth or the equivalent.

The invention may include a vacuum source that can use a solenoid to achieve vacuum.

The invention may include a pump that may use controls on both sides for bidirectional shaft motion to create vacuum.

Accordingly, while the invention has been described to a certain degree of particularity, it is implicitly understood that many changes may be made in the details of construction and the arrangement of components without straying from the scope and spirit of this disclosure. Changes, therefore, may be made in the combinations, operations, and arrangements of the various parts and elements described herein without departing from the spirit and scope of the invention.

The invention claimed is:

1. A prosthetic vacuum system comprising:
   a socket; and
   an electric vacuum pump in fluid communication with the socket, the electric vacuum pump comprising:
   a housing;
   a piston within the housing;
   a first one-way valve coupled to the piston;
   an end cap attached to a first end of the housing; and
   a second one-way valve in the end cap.

2. The vacuum system of claim 1, wherein the vacuum pump further comprises an electric actuator coupled to the piston.

3. The vacuum system of claim 2, further comprising a controller in signal communication with the vacuum pump.

4. The vacuum system of claim 3, further comprising a pressure sensor configured to sense a pressure in the socket.

5. The vacuum system of claim 4, wherein the controller is configured to activate the vacuum pump based on the sensed pressure.

6. The vacuum system of claim 2, further comprising a pylon attached to the socket, wherein the vacuum pump is located within the pylon.

7. The vacuum system of claim 2, wherein the housing is a pylon attached to the socket.

8. A prosthetic vacuum system for a socket of a prosthetic device, the vacuum system comprising:
   a housing;
   a piston within the housing;
   an electric actuator coupled to the piston;
   a first one-way valve coupled to the piston;
   an end cap attached to a first end of the housing;
   a second one-way valve in the end cap;
   a pressure sensor for sensing a pressure in the socket; and
   a controller in signal communication with the pressure sensor and the electric actuator,
   wherein the controller is configured to dynamically activate the electric actuator based on the sensed pressure.

9. The vacuum system of claim 8, further comprising a connecting rod attached to the piston.

10. A method of operating a prosthetic vacuum system, the method comprising:
    sensing a pressure level in a prosthetic socket;
    sending a signal to a controller based on the sensed pressure level;
    generating an activation signal based on the sensed pressure level;
    sending the activation signal to an electric vacuum pump; and
    moving a piston in a housing based on the activation signal, wherein moving the piston generates an air exchange through a first one-way valve coupled to the piston and also generates an air exchange through a second one-way valve located in an end cap attached to a first end of the housing.

11. The method of claim 10, wherein moving a piston comprises activating an electric actuator.

12. The method of claim 11, wherein the actuator is an electric linear actuator.

* * * * *